(12) United States Patent

Kauffman

(10) Patent No.: US 7,229,945 B2
(45) Date of Patent: Jun. 12, 2007

(54) PROCESS OF MAKING MIXED METAL OXIDE CATALYSTS FOR THE PRODUCTION OF UNSATURATED ALDEHYDES FROM OLEFINS

(75) Inventor: James W. Kauffman, Katy, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 142 days.

(21) Appl. No.: 10/741,383

(22) Filed: Dec. 19, 2003

(65) Prior Publication Data

US 2005/0137081 A1   Jun. 23, 2005

(51) Int. Cl.
  B01J 23/00  (2006.01)
  B01J 31/00  (2006.01)
  B01J 37/00  (2006.01)
  B01J 21/00  (2006.01)
  C08F 4/00   (2006.01)

(52) U.S. Cl. .................. 502/311; 502/104; 502/110; 502/111; 502/113; 502/117; 502/212; 502/248; 502/255; 502/312; 502/313; 502/314; 502/315; 502/316; 502/317; 502/318; 502/319; 502/320; 502/321; 502/322; 502/323

(58) Field of Classification Search ........... 502/104, 502/110, 111, 113, 117, 212, 248, 255, 311–323
See application file for complete search history.

(56) References Cited

U.S. PATENT DOCUMENTS

| 3,984,477 | A | * | 10/1976 | Kubo et al. ............. 568/479 |
| 4,259,211 | A | * | 3/1981 | Krabetz et al. ........... 502/178 |
| 4,438,217 | A | * | 3/1984 | Takata et al. ............ 502/205 |
| 4,511,671 | A |   | 4/1985 | Saito et al. |
| 4,537,874 | A | * | 8/1985 | Sato et al. .............. 502/311 |
| 4,556,731 | A |   | 12/1985 | Guttmann et al. |
| 4,816,603 | A |   | 3/1989 | Oh-Kita et al. |
| 4,837,191 | A | * | 6/1989 | Glaeser et al. ........... 502/202 |
| 4,916,103 | A |   | 4/1990 | Martan et al. |
| 5,166,119 | A |   | 11/1992 | Oh-Kita et al. |
| 5,198,581 | A | * | 3/1993 | Kawajiri et al. ........... 562/546 |
| 5,245,083 | A |   | 9/1993 | Matsuura |
| 5,276,178 | A |   | 1/1994 | Onodera et al. |
| 5,532,199 | A |   | 7/1996 | Watanabe et al. |
| 5,602,280 | A |   | 2/1997 | Nagai et al. |
| 5,728,894 | A |   | 3/1998 | Nagano et al. |
| 5,856,259 | A |   | 1/1999 | Watanabe et al. |
| 5,929,275 | A | * | 7/1999 | Wada et al. ............. 562/545 |
| 5,959,143 | A | * | 9/1999 | Sugi et al. .............. 562/534 |
| 6,028,220 | A |   | 2/2000 | Wada et al. |
| 6,429,332 | B1 | * | 8/2002 | Tanimoto et al. .......... 562/532 |
| 6,509,508 | B2 | * | 1/2003 | Kimura et al. ............ 568/479 |
| 6,596,897 | B1 | * | 7/2003 | Guan et al. ............. 558/323 |
| 6,632,772 | B2 | * | 10/2003 | Lee et al. ............... 502/248 |
| 6,693,059 | B2 | * | 2/2004 | Lin ..................... 502/308 |
| 6,784,134 | B2 | * | 8/2004 | Kasuga et al. ........... 502/182 |
| 6,794,539 | B2 | * | 9/2004 | Unverricht et al. ........ 562/535 |
| 6,797,839 | B1 | * | 9/2004 | Hibst et al. ............. 562/532 |
| 6,881,702 | B2 | * | 4/2005 | Arnold et al. ........... 502/311 |
| 6,924,387 | B1 | * | 8/2005 | Chang et al. ............ 558/323 |
| 6,946,422 | B2 | * | 9/2005 | Stevenson et al. ......... 502/311 |
| 2004/0192973 | A1 | * | 9/2004 | Liang et al. ............ 568/470 |

* cited by examiner

*Primary Examiner*—Cam N. Nguyen
(74) *Attorney, Agent, or Firm*—Jim Wheelington

(57) ABSTRACT

The present invention is for a process for making a catalyst for production of unsaturated aldehydes, such as methacrolein, by gas phase catalytic oxidation of olefins, such as isobutylene, said catalyst containing oxides of molybdenum, bismuth, iron, cesium, tungsten, cobalt, nickel, antimony, magnesium and zinc. The process is a two-part synthesis of the catalyst with the water insoluble components in one part and the water soluble components in the other part. The water insoluble components are co-precipitated to form an intermediate catalyst precursor of a precipitated support incorporating oxides of the metal components. The intermediate catalyst precursor is filtered and washed to remove nitrates. The intermediate catalyst precursor is slurried with the remaining water soluble components. A final catalyst precursor is formed by removing the water and incorporating the water soluble components. This two-part process reduces the amount of nitrates in the final catalyst precursor.

25 Claims, No Drawings

PROCESS OF MAKING MIXED METAL OXIDE CATALYSTS FOR THE PRODUCTION OF UNSATURATED ALDEHYDES FROM OLEFINS

BACKGROUND OF THE INVENTION

1. Field of the Invention

This invention relates to a process of making a mixed metal oxide catalyst containing oxides of molybdenum, bismuth, iron, cesium, antimony and other metals for the production of unsaturated aldehydes from olefins, such as methacrolein by gas phase catalytic oxidation of isobutylene in the presence of air or another gas containing molecular oxygen.

2. Description of the Prior Art

Typically, the catalyst for oxidation of isobutylene to methacrolein is a mixed metal oxide prepared by mixing compounds containing the desired elements in a solution or a suspension and drying the resulting concentrate. Thereafter, the dried product is calcined. The calcined product may be ground or formed to a mesh size suitable for use. The prepared catalyst can be prepared with a specific surface area. The catalysts may be supported on a suitable carrier, such as silica, silica-containing materials, silicon carbide, alumina and the like, in order to improve the physical properties of the catalysts. Many methods of making catalysts for use in the production of acrolein or methacrolein by catalytic vapor phase oxidation of propylene or isobutylene have been disclosed.

U.S. Pat. No. 4,816,603 discloses a catalyst for production of methacrolein and methacrylic acid of the formula:

$$Mo_aW_bBi_cFe_dNi_eSb_fX_gY_hZ_iA_jO_k$$

where X is potassium, rubidium and/or cesium, Y is phosphorus, sulfur, silicon, selenium, germanium and/or boron, Z is zinc and/or lead, A is magnesium, cobalt, manganese and/or tin, a is 12, b is 0.001 to 2, c is 0.01 to 3, d is 0.01 to 8, e is 0.01 to 10, f is 0.01 to 5, g is 0.01 to 2, h is 0 to 5, i is 0.01 to 5, j is 0 to 10 and k is sufficient to satisfy the valences. The method of preparation disclosed was that solution A of ammonium molybdate, ammonium paratungstate and rubidium nitrate and solution B of bismuth nitrate, ferric nitrate, nickel nitrate, magnesium nitrate and zinc nitrate were formed, solution B was added to solution A to form a slurry and antimony trioxide was added to the slurry.

U.S. Pat. No. 4,511,671 discloses a catalyst for manufacturing methacrolein of the formula:

$$Mo_aW_bBi_cFe_dA_eB_fC_gD_hO_x$$

where A is at least one of nickel and/or cobalt; B is at least one of alkali metals, alkaline earth metals and/or thallium; C is at least one of phosphorus, tellurium, antimony, tin, cerium, lead, niobium, manganese and/or zinc; D is at least one of silicon, aluminum, zirconium, and/or titanium; a is 12, b is 0 to 10, c is 0.1 to 10, d is 0.1 to 20, e is 2 to 20, f is 0 to 10, g is 0 to 4, h is 0 to 30 and x is determined by the atomic valences. The method of preparation disclosed was that cobalt nitrate and ferric nitrate were dissolved in water and separately bismuth nitrate was dissolved in water and nitric acid. These two solutions were mixed and then added to another solution of ammonium paramolybdate and ammonium paratungstate dissolved in water. A solution of cesium nitrate dissolved in water and a solution of silica sol were also added.

U.S. Pat. No. 4,556,731 discloses a catalyst for production of methacrolein and methacrylic acid of the formula:

$$A_aB_bFe_cX_dM_eMO_{12}O_x$$

where A is an alkali metal, such as potassium, rubidium, cesium or mixtures thereof, thallium, silver or mixtures thereof, B is cobalt, nickel, zinc, cadmium, beryllium, calcium, strontium, barium, radium or mixtures thereof, X is bismuth, tellurium or mixtures thereof and M is (1) Cr+W, Ge+W, Mn+Sb, Cr+P, Ge+P, Cu+W, Cu+Sn, Mn+Cr, Pr+W, Ce+W, Sn+Mn, Mn+Ge or combinations thereof, (2) Cr, Sb, Ce, Pn, Ge, B, Sn, Cu or combinations thereof, or (3) Mg+P, Mg+Cu, Mg+Cr, Mg+Cr+W, Mg+W, Mg+Sn or combinations thereof, a is 0 to 5, b is 0 to 20, c is 0 to 20, d is 0 to 20, e is 0.01 to 12 and x satisfies the valence requirements. The method of preparation disclosed was that solution A of ammonium molybdate, phosphoric acid, water and silica sol and solution B of ferric nitrate, bismuth nitrate, nickel nitrate, cobalt nitrate, cobalt nitrate and potassium nitrate were prepared and then solution B was added to solution A.

U.S. Pat. No. 5,245,083 discloses a catalyst for preparing methacrolein of a mixture of composition (1) of the formula:

$$Mo_aBi_bFe_cX_dZ_fO_g$$

where X is Ni and/or Co, Z is at least one of W, Be, Mg, S, Ca, Sr, Ba, Te, Se, Ce, Ge, Mn, Zn, Cr, Ag, Sb, Pb, As, B, P, Nb, Cu, Cd, Sn, Al, Zr and Ti, a is 12 b is 0.1 to 10, c is 0 to 20, d is 0 to 20, f is 0 to 4 and g satisfies the valence requirement and composition (2) of the formula:

$$A_mMo_nO_p$$

where A is at least one of K, Rb and Cs, m is 2, n is 1 to 9 and p is 3n+1. The method of preparation was that solution A of ammonium paramolybdate in water, solution B of cobalt nitrate and ferric nitrate in water, solution C of bismuth nitrate in aqueous nitric acid were prepared and solution B and solution C were added to solution A. Separately, ammonium molybdate was dissolved in water to form a solution to which cesium nitrate and nitric acid were added. The two resulting compositions were mixed to form a catalyst. In a comparative example, the cesium nitrate was dissolved in solution A such that only one composition was formed into a catalyst.

U.S. Pat. No. 4,537,874 discloses a catalyst for production of unsaturated aldehydes of the formula:

$$Bi_aW_bFe_cMo_dA_eB_fC_gD_hO_x$$

where A is nickel and/or cobalt, B is at least one of alkali metal, alkaline earth metals and thallium, C is at least one of phosphorus, arsenic, boron, antimony, tin, cerium, lead and niobium, D is at least one of silicon, aluminum, zirconium and titanium, a is 0.1 to 10.0, b is 0.5 to 10.0, c is 0.1 to 10.0, d is 12, e is 2.0 to 20.0, f is 0.001 to 10.0, g is 0 to 10.0 and h is 0 to 30 and x satisfies the valence requirement. The ratio of a/b is 0.01 to 6.0 so that bismuth is combined very stably with tungsten and compounds such as bismuth trioxide and bismuth molybdate are not formed. The method of preparation disclosed was that bismuth nitrate was dissolved in water and nitric acid to form a solution to which aqueous ammonia was added to obtain a white precipitate which was collected as a yellow powder. Separately, aqueous solutions of cobalt nitrate, ferric nitrate, silica sol and potassium nitrate were added to an aqueous solution of ammonium molybdate to form a suspension to which the yellow powder was added. In one example, an aqueous solution of sodium tungstate was added to the bismuth nitrate solution.

U.S. Pat. No. 5,728,894 discloses a catalyst for producing methacrolein of the formula:

where A is Co or a mixture of Co and Mg having an atomic ratio of not more than 0.7, B is Rb, Cs or a mixture thereof, a is 0 to 8, b is 0 to 8, c is 0 to 1.2, d is 0 to 2.5, e is 1.0 to 12, f is 0 to 2.0 and x satisfies the valence requirement. The relative atomic ratio of iron to bismuth and cerium should be $0<d/(a+b+d)\leq 0.9$. The relative atomic ratio of bismuth, cerium and potassium should be $0.05\leq b/(a+b+c)\leq 0.7$. The relative atomic ratio of potassium to bismuth and cerium should be $0<c/(a+b+c)\leq 0.4$. Bismuth, cerium, potassium, iron and cobalt are indispensable elements for the disclosed invention. The method of preparation disclosed is that solution A of ammonium heptamolybdate and water and solution B of bismuth nitrate, cerium nitrate, iron nitrate, cesium nitrate, potassium nitrate and cobalt nitrate were prepared and solution A and solution B were mixed.

U.S. Pat. No. 4,916,103 discloses a catalyst for oxidation of propylene to acrolein and acrylic acid containing molybdenum, bismuth, iron, cobalt or nickel, phosphorus; at least one of arsenic, antimony, tin, thallium, tungsten, an alkaline earth metal, zinc and/or chromium; and at least one of sodium, potassium, rubidium, cesium and/or indium. The method of preparation disclosed was that ammonium heptamolybdate was dissolved in water and potassium hydroxide to form a solution to which iron molybdate, cobalt nitrate, bismuth tungstenate and silica sol solution were added.

U.S. Pat. No. 5,166,119 discloses a catalyst for producing methacrolein and methacrylic acid containing molybdenum, tungsten, bismuth, iron, antimony; at least one of nickel and/or cobalt; at least one of cesium and/or thallium; at least one of magnesium, manganese, zinc, barium and/or chromium; and at least one of phosphorus, boron, sulfur, silicon, cerium, potassium and/or rubidium. The method of preparation disclosed was that solution A of ammonium molybdate and cesium nitrate in water and solution B of bismuth nitrate, ferric nitrate, nickel nitrate, cobalt nitrate and magnesium nitrate in nitric acid and water were prepared and solution B was added to solution A. In one example solution B was of bismuth nitrate and cobalt nitrate and there was an additional solution C of ferric nitrate and zinc nitrate which was added after solution B.

U.S. Pat. No. 5,276,178 discloses a catalyst for producing methacrolein and methacrylic acid containing molybdenum, tungsten, bismuth, iron; at least one of nickel and/or cobalt; at least one of alkali metal and/or thallium; at least one of alkaline earth metals; at least one of phosphorus, tellurium, antimony, tin, cerium, lead, niobium, manganese, arsenic and/or zinc; and at least one of silicon, aluminum, titanium and/or zirconium. The method of preparation disclosed is that cobalt nitrate and ferric nitrate were dissolved in water, bismuth nitrate was dissolved in aqueous nitric acid, cesium nitrate was dissolved in water and ammonium paramolybdate and ammonium paratungstate were dissolved in water. The first three solutions and silica sol were added to the last solution. A second catalyst with a less amount of cesium was prepared and used with the first catalyst in the isobutylene oxidation. In another example, no ammonium paratungstate was used, thallous nitrate and strontium nitrate were used in place of cesium nitrate, tellurium oxide, lead nitrate and zinc nitrate were added and titanium dioxide was used in place of silica sol. In another example, potassium nitrate, barium nitrate and beryllium nitrate were used in place of cesium nitrate, antimony trioxide and manganese nitrate were added and zirconium nitrate was used in place of silica sol.

U.S. Pat. No. 5,532,199 discloses a catalyst for producing acrolein and acrylic acid or methacrolein and methacrylic acid containing molybdenum, bismuth, iron; at least one of nickel and/or cobalt; at least one of magnesium, zinc, manganese, tin and/or lead; at least one of phosphorus, boron, sulfur, tellurium, silicon, selenium, germanium, cerium, niobium, aluminum, titanium, zirconium, tungsten and/or antimony; and at least one of potassium, sodium, rubidium, cesium and/or thallium. The method of preparation disclosed was that ammonium paramolybdate, ammonium paratungstate, cesium nitrate and antimony trioxide were added to water to form a first solution and bismuth nitrate, ferric nitrate, nickel nitrate, cobalt nitrate, magnesium nitrate, zinc nitrate and boric acid were added to nitric acid and water to form a second solution which was added to the first solution.

U.S. Pat. No. 5,602,280 discloses a catalyst for producing acrolein and acrylic acid or methacrolein and methacrylic acid containing molybdenum, bismuth, iron; at least one of nickel and/or cobalt; at least one of manganese, zinc calcium, magnesium, tin and/or lead; at least one of phosphorus, boron, arsenic, tellurium, tungsten, antimony and/or silicon; and at least one of potassium, rubidium, cesium and/or thallium. The method of preparation is that solution A of ammonium molybdate and silica sol in water, solution B of nickel nitrate (or cesium nitrate), cobalt nitrate, ferric nitrate and thallium nitrate in water and solution C of bismuth nitrate in nitric acid and water were prepared and a mixture of solution B and solution C was added to solution A.

U.S. Pat. No. 5,856,259 discloses a catalyst for producing methacrolein and methacrylic acid containing molybdenum, bismuth, iron; at least one of nickel and/or cobalt; at least one of magnesium, zinc, manganese, tin and/or lead; at least one of phosphorus, boron, sulfur, tellurium, silicon, germanium, cerium niobium, titanium, zirconium, tungsten and antimony; and at least one of potassium, sodium, rubidium, cesium and/or thallium. The method of preparation was that a first solution of ammonium paramolybdate, antimony trioxide, titanium dioxide and tellurium dioxide in water, a second solution of bismuth nitrate, ferric nitrate, nickel nitrate, cobalt nitrate, magnesium nitrate and cesium nitrate in aqueous nitric acid were prepared and the second solution was added to the first solution. In another example, a first solution of ammonium paramolybdate, silicon dioxide and ammonium paratungstate in water and a second solution of bismuth nitrate, ferric nitrate, nickel nitrate, cobalt nitrate, zinc nitrate, cerium nitrate, rubidium nitrate and potassium nitrate in aqueous nitric acid were prepared and the second solution was added to the first solution. In another example, a first solution of ammonium paramolybdate and zirconium dioxide and a second solution of phosphoric acid, bismuth nitrate, ferric nitrate, cobalt nitrate, manganese nitrate, lead nitrate, cesium nitrate, sodium nitrate in aqueous nitric acid were prepared and the second solution was added to the first solution. In another example, a first solution of ammonium paramolybdate, tin oxide and germanium dioxide in water and a second solution of boric acid, sulfuric acid, bismuth nitrate, ferric nitrate, nickel nitrate, cobalt nitrate, zinc nitrate, thallium nitrate and cesium nitrate in aqueous nitric acid were prepared and the second solution was added to the first solution.

U.S. Pat. No. 6,028,220 discloses a catalyst for producing acrolein and acrylic acid containing molybdenum, bismuth, nickel, cobalt, iron; at least one of tin, zinc, tungsten, chromium, manganese, magnesium, antimony and/or titanium; and at least one of potassium, rubidium, thallium and/or cesium. The method of preparation disclosed was that solution A of ammonium molybdate and potassium nitrate in water and solution B of cobalt nitrate, nickel nitrate and ferric nitrate in water and solution C of bismuth nitrate in water and nitric acid were prepared and a mixture of solution B and solution C was added to solution A.

Prior art discloses different methods of making mixed metal oxide catalysts which contain molybdenum, bismuth, iron, cesium and other metals for the production of methacrolein. The advantages of a particular method of making or order of addition wherein the water soluble compounds and the water insoluble compounds are prepared separately and then mixed to form the catalyst has not been disclosed.

SUMMARY OF THE INVENTION

The present invention is for a process of making a catalyst of the general formula:

$$Mo_{12}Bi_aW_bFe_cCs_gM_mM'_{m'}O_x$$

wherein M is one or more of antimony, phosphorus, boron, sulfur, silicon, aluminum, titanium, tellurium, vanadium, zirconium and niobium and M' is one or more selected from cobalt, nickel, magnesium, zinc, potassium, rubidium, thallium, manganese, barium, chromium, cerium, tin, lead, cadmium and copper, a is in the range from 0.1 to 1.5, b is 0 to 9, c is in the range from 0.2 to 5.0, g is in the range from 0.1 to 1.5, m is in the range from 0 to 9, m' is from 0 to 9 and x is determined by the valences of the other components.

The process of making the catalyst is generally to mix the metal compounds of molybdenum, bismuth, iron, cesium, tungsten, M and M' in a solution or slurry and precipitate a catalyst precursor which is calcined to form a mixed metal oxide catalyst. The metal compounds may be salts (e.g., nitrates, halides, ammonium, organic acid, inorganic acid), oxides, hydroxides, carbonates, oxyhalides, sulfates and other groups which may exchange with oxygen under high temperatures so that the metal compounds become metal oxides. It is preferable that the molybdenum compound and the tungsten compound are ammonium salts, that the bismuth compound, the ferric compound, the nickel compound, the cobalt compound, the magnesium compound, the zinc compound, the cesium compound, the potassium compound, the rubidium compound, the thallium compound, the manganese compound, the barium compound, the chromium compound, the boron compound, the sulfur compound, the silicon compound, the aluminum compound, the titanium compound, the cerium compound, the tellurium compound, the tin compound, the vanadium compound, the zirconium compound, the lead compound, the cadmium compound, the copper compound and the niobium compound are nitrates, oxides or acids and the antimony compound is an oxide.

The process of the present invention is a two-part synthesis of the catalyst with the water insoluble components in one part and the water soluble components in the other part. The water insoluble components are co-precipitated to form an intermediate catalyst precursor of a precipitated support incorporating oxides of the metal components. The intermediate catalyst precursor is filtered and washed to remove nitrates. The intermediate catalyst precursor is slurried with the remaining water soluble components. A final catalyst precursor is formed by removing the water and incorporating the water soluble components.

This two-part process reduces the amount of nitrates in the final catalyst precursor. During calcination of the catalyst precursor to form the catalyst, nitrates decompose in an exothermic reaction that generates "hot spots" which can damage and deactivate the catalyst. Nitrates can also generate gases which are environmentally undesirable.

DESCRIPTION OF EMBODIMENTS OF THE INVENTION

The present invention is for a process for making catalyst for producing acrolein or methacrolein by oxidation of propylene or isobutylene. The exact chemical structure of the catalysts of this invention is not known. However, it is presumed that the catalyst is a homogeneous mixture of the oxides and/or complex oxides of all the components.

The catalyst is a mixed metal oxide of the formula:

$$Mo_{12}Bi_aW_bFe_cCs_gM_mM'_{m'}O_x$$

wherein M is one or more of antimony, phosphorus, boron, sulfur, silicon, aluminum, titanium, tellurium, vanadium, zirconium and niobium and M' is one or more selected from cobalt, nickel, magnesium, zinc, potassium, rubidium, thallium, manganese, barium, chromium, cerium, tin, lead, cadmium and copper, a is in the range from 0.1 to 1.5, b is 0 to 9, c is in the range from 0.2 to 5.0, g is in the range from 0.1 to 1.5, m is in the range from 0 to 9, m' is from 0 to 9 and x is determined by the valences of the other components.

Most preferably, the catalyst is of the formula:

$$Mo_{12}Bi_aW_bFe_cCo_dNi_eSb_fCs_gMg_hZn_iO_x$$

wherein b is 0 to 4, d is 0 to 9, e is 0 to 9, f is 0 to 2.0, h is 0 to 1.5 and i is 0 to 2.0.

The process of making the catalyst is generally to form a solution or slurry of the metal compounds and precipitate a catalyst precursor which is calcined to form a mixed metal oxide catalyst. The metal compounds may be salts (e.g., nitrates, halides, ammonium, organic acid, inorganic acid), oxides, hydroxides, carbonates, oxyhalides, sulfates and other groups which may exchange with oxygen under high temperatures so that the metal compounds become metal oxides. It is more preferred that the molybdenum compound and the tungsten compound are ammonium salts, such as ammonium paramolybdate or ammonium molybdate and ammonium paratungstate or ammonium tungstate, respectively, that the bismuth, iron, cobalt, nickel, cesium, magnesium, zinc, phosphorus, potassium, rubidium, thallium, manganese, barium, chromium, boron, sulfur, silicon, aluminum, titanium, cerium, tellurium, tin, vanadium, zirconium, lead, cadmium, copper and niobium compounds are nitrates, oxides or acids and that the antimony compound is an oxide, such as antimony oxide or antimony trioxide. For bismuth, iron, cesium, cobalt, nickel, magnesium and zinc compounds, it is preferred that they are nitrates.

The present invention depends on a particular order of addition of the components.

An example of making the catalyst of the claimed invention is to form a slurry of an ammonium salt of molybdenum, such as ammonium paramolybdate or ammonium molybdate, optionally, an ammonium salt of tungsten, such as ammonium paratungstate or ammonium tungstate, a bismuth nitrate dissolved in an acid, an iron nitrate and a cesium nitrate and to form a solution of a cobalt nitrate, a nickel nitrate, a magnesium nitrate and a zinc nitrate in water to form a divalent metal nitrate solution. The slurry is co-precipitated to form an intermediate catalyst precursor of a precipitated support incorporating oxides of the water insoluble metal components. Precipitation may occur at a temperature in the range of from 40° C. to 100° C. or at a temperature in the range of from 60° C. to 95° C. The intermediate catalyst precursor is filtered and washed to remove nitrates. The intermediate catalyst precursor is slurried with the divalent metal nitrate solution the cobalt nitrate, the nickel nitrate, the magnesium nitrate and the zinc nitrate. Antimony oxide may be added as a solid. The slurry may be aged for 2 to 24 hours, preferably 8 to 18 hours, most preferably 5 to 10 hours. The liquid of the slurry is removed by evaporation and the solid precipitate is dried and calcined to obtain a catalyst. The liquid may be removed and the solid precipitate dried at the same time by spray drying. The liquid may be evaporated at a temperature of 50° to 125° C.

Drying of the catalyst precursor may be in air or an inert gas and in an oven or a spray dryer. Preferably, drying is in an oven in air at a temperature of 100–150° C. for 2–5 hours One purpose of calcination of the catalyst precursor is to obtain an oxide of the metal components. The catalyst precursor may be calcined at a temperature of 200–600° C. for 1–12 hours. Calcination may be in two stages, one at a temperature of 150–400° C. for 1–5 hours and another at a temperature of 460–600° C. for 4–8 hours. For a two-stage calcination, preferably, the first is at a temperature of 290–310° C. for 2 hours and second at a temperature of 460–500° C. for 6 hours with an increase in temperature at 0.5 to 20° C./min, preferably 5 to 10° C./min. Denitrification may occur in the first step. In the alternative, calcination is in one stage at a temperature of 450–500° C. for 1–4 hours with a temperature ramp of 0.5 to 20° C./min, preferably 5 to 10° C./min, from ambient temperature instead of an initial step or denitrification. Calcination may be done in a high temperature oven or kiln.

The catalyst may be processed by sieving, forming and other means known in the art to obtain catalyst particles of a certain size. Desired particle size and particle size distribution are related to the design of the reactor (size, shape, configuration, etc.), to the pressure drop intended for the process and to the process flow. For a two stage calcination, the catalyst may be sieved or formed after the first stage calcination and before the second stage calcination. In a commercial process the catalyst precursor may be sieved and formed after spray drying and before calcination.

The X-ray diffraction pattern of the mixed metal oxide catalyst of the present invention is not substantially different from catalysts made by other processes. The catalyst compositions of the Examples above have a characteristic X-ray diffraction having diffraction peaks at the diffraction angles of 2θ, measured by using Cu Kα radiation, at about 9.6, 14.2, 23.0, 26.7 and 28.0 degrees. X-ray diffraction patterns of the catalysts of the Comparative Examples show the same diffraction peaks.

The catalyst of the present invention may be used as an unsupported catalyst or a supported catalyst. The surface area of an unsupported catalyst is from 0.1 to 150 m$^2$/g, preferably from 1 to 20 m$^2$/g. If supported, the support should be an inert solid which is chemically unreactive with any of the active components of the catalyst and is preferably silica, alumina, niobia, titania, zirconia or mixtures thereof. The catalyst may be affixed to the support by methods known in the art, including incipient wetness, slurried reactions and spray drying. The catalyst is not limited by shape, size or particle distribution and may be formed as appropriate for the reaction vessel in the process. Examples are powder, granules, spheres, cylinders, saddles, etc.

The catalyst is used in the gas phase catalytic oxidation of a feedstock gas comprising propylene or isobutylene, oxygen, water and an inert gas, such as nitrogen, to produce acrolein or methacrolein. Oxygen may be supplied in the pure form or in an oxygen containing gas, such as air or as an oxygen-diluent gas mixture. The diluent gas may be nitrogen, a hydrocarbon which is gaseous under the process conditions or carbon dioxide. The reaction temperature is preferably from 250–450° C., most preferably 370–410° C. The reactor may be a fixed bed or a fluidized bed reactor. Reaction pressure may be from 0 to 100 psig. Space velocity may be from 800 to 8000 hr$^{-1}$.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

43.57 g of ammonium paramolybdate tetrahydrate and 1.66 g of ammonium paratungstate hydrate were added to about 90 mL of water and heated from room temperature to 95° C. over 58 minutes to dissolve the metal salts.

Separately, 9.97 g of bismuth nitrate hydrate and 19.93 g of ferric nitrate hydrate were dissolved in a solution of 1.84 g concentrated nitric acid and 9.4 g of water.

The bismuth, iron solution was added to the molybdate solution over a 30 minute period.

2.41 g of cesium nitrate was added about 16 minutes after the bismuth solution addition.

2.11 g of antimony trioxide was then added 3 minutes later.

The solution was digested for about 10 hours at 95° C. The yellow precipitate that formed was filtered and washed with about 224 mL of water. The washed filter cake was slurried with about 100 mL of water.

Separately, 23.92 g nickel nitrate hydrate, 12.03 g cobalt nitrate hydrate, 2.64 g magnesium nitrate hydrate, and 3.24 g zinc nitrate hydrate was dissolved in about 100 mL of water and added to the slurry. The slurry was well mixed.

The slurry was evaporated in a crucible at 50° C. to a wet paste. The paste was dried at 120° C. for 2 hours in a 1.2 ft.3 muffle furnace with ~5 lpm airflow. The dried paste was calcined at about 480° C. for 2 hour with a 10° C./min ramp and 200 mL/min airflow in a rotary furnace. The catalyst was sized for reactor testing.

EXAMPLE 2

43.58 g of ammonium paramolybdate tetrahydrate and 1.65 g of ammonium paratungstate hydrate were added to about 87 mL of water. The solution was agitated and heated from room temperature to 95° C. to dissolve the metal salts in about 60 minutes.

Separately, 9.97 g of bismuth nitrate hydrate were dissolved in a solution of 1.83 g concentrated nitric acid and 9.3 g of water.

Separately, 19.94 g of ferric nitrate hydrate, 23.91 g nickel nitrate hydrate, 12.04 g cobalt nitrate hydrate, 2.64 g magnesium nitrate hydrate, and 3.24 g zinc nitrate hydrate was dissolved in about 86 mL of water.

The bismuth nitrate solution was added to the ferric nitrate solution with agitation. The metal nitrate solution was then added to the molybdate solution with agitation (about 220 rpm) over about 31 minutes in a drop wise manner.

The temperature of the solution dropped to 85° C. during addition of the metal nitrate solution and then it increased back to 95° C. after addition.

Immediately after addition of the metal nitrate solution, 2.4 g of solids cesium nitrate was added all at once. Then 2.12 g of solid antimony trioxide was added to the slurry over a 5 minute period.

The solution was digested for about 6 hours at 95° C.

After digestion the solution was boiled down to a paste. The paste was dried at about 120° C. for two hours in a 1.2 ft.$^3$ muffle furnace with ~5 lpm airflow.

The cake was calcined at 480° C. for 2 hour with a 10° C./min ramp and 200 mL/min airflow in a rotary furnace and sized to load into the test reactor.

The nitrate contents listed below are for the catalyst precursor cake before denitrification and calcination obtained by ion chromatography. Both samples were analyzed by a single aqueous extraction followed by filtration. Both samples were dried for 2 hours at 120° C. in air to a dried cake.

Example: 16.0% by weight nitrates

Comparative Example: 22.8% by weight nitrates

The theoretical amount of nitrates is about 33%. The difference between 22.8% and 33% is probably due to loss during drying and nitrates remaining in the filter cake from a single wash.

The nitrates are reduced by filtration about 30%. The amount of nitrate removed by filtration will increase when the amount lost during drying is take into account. Any nitrate loss during drying is also considered undesirable because of the requirement to scrub the drier effluent gases and the possibility of nitrate accumulation in drier bag houses which have resulted in explosions Obviously, numerous modifications and variations of the present invention are possible in light of the above teachings. It is therefore to be understood that within the scope of the appended claims, the invention may be practiced otherwise than as specifically described herein.

What is claimed is:

1. A process for preparing catalyst for the oxidation of an olefin to an unsaturated aldehyde comprising:
    a) forming a slurry of water insoluble components of molybdenum, bismuth, iron, cesium, tungsten and M in water or acid, wherein M is one or more of antimony, phosphorus, boron, sulfur, silicon, aluminum, titanium, tellurium, vanadium, zirconium or niobium, and wherein the bismuth, iron and cesium components are nitrates;
    b) precipitating an intermediate catalyst precursor;
    c) removing liquid from the intermediate catalyst precursor;
    d) washing the intermediate catalyst precursor;
    e) drying the intermediate catalyst precursor;
    f) contacting the intermediate catalyst precursor with a solution of water soluble M' components, wherein M' is one or more of cobalt, nickel, magnesium, zinc, potassium, rubidium, thallium, manganese, barium, chromium, cerium, tin, lead, cadmium or copper, to form a final catalyst precursor;
    g) removing water from the final catalyst precursor;
    h) drying the final catalyst precursor; and
    i) calcining the final catalyst precursor to form oxides of the metals to form a catalyst.

2. The process of claim 1 wherein M' is magnesium.

3. The process of claim 2 wherein said magnesium component is a nitrate.

4. The process of claim 1 wherein M' is cobalt component.

5. The process of claim 4 wherein said cobalt component is a nitrate.

6. The process of claim 1 wherein M' is nickel.

7. The process of claim 6 wherein said nickel component is a nitrate.

8. The process of claim 1 wherein M is antimony.

9. The process of claim 8 wherein said antimony component is an oxide.

10. The process of claim 1 wherein M' is zinc.

11. The process of claim 10 wherein said zinc component is a nitrate.

12. The process of claim 1 wherein the catalyst has an X-ray diffraction pattern of diffraction peaks at the diffraction angles of 2θ, measured by using Cu Kα radiation, at 9.6, 14.2, 23.0, 26.7 and 28.0 degrees.

13. The process of claim 1 wherein precipitation occurs at a temperature in the range of from 40° C. to 100° C.

14. The process of claim 13 wherein precipitation occurs at a temperature in the range of from 60° C. to 95° C.

15. The process of claim 1 additionally comprising aging for 2 to 24 hours before the liquid is removed.

16. The process of claim 15 wherein the aging is for 8 to 18 hours.

17. The process of claim 16 wherein the aging is for 5 to 10 hours.

18. The process of claim 1 wherein the final catalyst precursor is calcined at a temperature of 200–600° C. for 1–12 hours.

19. The process of claim 18 wherein the final catalyst precursor is calcined in two stages, one at a temperature of 150–400° C. for 1–5 hours and another at a temperature of 460–600° C. for 4–8 hours.

20. The process of claim 19 wherein the two-stage calcination is first at a temperature of 290–310° C. for 2 hours and second at a temperature of 460–500° C. for 6 hours.

21. The process of claim 20 wherein the temperature is increased from the first stage to the second stage at 0.5 to 20° C./min.

22. The process of claim 21 wherein the temperature is increased at 5 to 10° C./min.

23. The process of claim 1 wherein the final catalyst precursor is calcined in one stage at a temperature of 450–500° C. for 1–4 hours.

24. The process of claim 23 wherein the temperature is increased from ambient to the calcination temperature at 0.5 to 20° C./min.

25. The process of claim 24 wherein the temperature is increased at 5 to 10° C./min.

* * * * *